United States Patent
Kondziolka et al.

(10) Patent No.: US 11,253,726 B2
(45) Date of Patent: Feb. 22, 2022

(54) METHOD TO SELECT RADIATION DOSAGE FOR TUMOR TREATMENT BASED ON CELLULAR IMAGING

(71) Applicant: NEW YORK UNIVERSITY

(72) Inventors: Douglas Kondziolka, New York, NY (US); Timothy Shepherd, Bronxville, NY (US)

(73) Assignee: New York University, New York, NY (US)

( * ) Notice: Subject to any disclaimer, the term of this patent is extended or adjusted under 35 U.S.C. 154(b) by 647 days.

(21) Appl. No.: 15/493,014

(22) Filed: Apr. 20, 2017

(65) Prior Publication Data

US 2017/0216624 A1 Aug. 3, 2017

Related U.S. Application Data

(63) Continuation-in-part of application No. PCT/US2015/056263, filed on Oct. 19, 2015.
(Continued)

(51) Int. Cl.
*A61N 5/10* (2006.01)
*A61B 6/03* (2006.01)
(Continued)

(52) U.S. Cl.
CPC .......... *A61N 5/1039* (2013.01); *A61B 5/0036* (2018.08); *A61B 5/055* (2013.01); *A61B 6/032* (2013.01); *A61B 6/037* (2013.01); *A61B 6/507* (2013.01); *A61B 6/5217* (2013.01); *A61N 5/1031* (2013.01); *G01R 33/56341* (2013.01)

(58) Field of Classification Search
CPC ....... A61B 6/507; A61B 5/4836; A61B 5/055; A61B 6/037; A61B 6/5217; A61B 6/032; G01R 33/56341; A61N 5/1031; A61N 5/1039
See application file for complete search history.

(56) References Cited

U.S. PATENT DOCUMENTS 6,228,540 B1 * 5/2001 Kobayashi .............. G03F 7/168
430/5
6,507,639 B1 1/2003 Popescu
(Continued)

OTHER PUBLICATIONS

International Search Report and Written Opinion for Application No. PCT/US2015/056263, dated Jan. 14, 2016, 8 pages.
(Continued)

*Primary Examiner* — Charles A Marmor II
*Assistant Examiner* — Joshua Daryl D Lannu
(74) *Attorney, Agent, or Firm* — Foley & Lardner LLP (57) ABSTRACT

Methods, systems, and apparatuses are disclosed for radiation treatment of tumors based at least in part on patient-specific imaging information. The methods, systems and apparatuses include computer programs encoded on computer-readable media. The methods include acquiring imaging information relating to a target to be treated. The imaging information is non-anatomic imaging information relating to the target acquired from at least one imaging marker that reflects at least one of the metabolic, physiological and histological features of the target. The methods further include computing a radiation dose based at least on the imaging information.

18 Claims, 4 Drawing Sheets

Related U.S. Application Data (60) Provisional application No. 62/066,265, filed on Oct. 20, 2014.

(51) Int. Cl.
    *A61B 6/00*     (2006.01)
    *A61B 5/055*     (2006.01)
    *A61B 5/00*     (2006.01)
    *G01R 33/563*     (2006.01)

(56) References Cited

U.S. PATENT DOCUMENTS

| | | | |
|---|---|---|---|
| 8,812,240 B2* | 8/2014 | Yu | G06T 11/00 702/19 |
| 2006/0074292 A1* | 4/2006 | Thomson | A61N 5/1049 600/411 |
| 2006/0241375 A1* | 10/2006 | Van Den Brink | G01R 33/56341 600/410 |
| 2007/0043286 A1 | 2/2007 | Lu et al. | |
| 2009/0052623 A1 | 2/2009 | Tome et al. | |
| 2009/0208422 A1* | 8/2009 | Mardor | A61K 49/1824 424/9.364 |
| 2009/0234626 A1* | 9/2009 | Yu | G06N 20/00 703/11 |
| 2011/0210261 A1* | 9/2011 | Maurer, Jr. | A61N 5/1067 250/393 |
| 2011/0229003 A1* | 9/2011 | Yang | G06T 7/0012 382/131 |
| 2013/0077752 A1 | 3/2013 | Zankowski | |
| 2013/0245425 A1 | 9/2013 | Dempsey | |
| 2013/0329973 A1* | 12/2013 | Cao | A61B 5/0033 382/128 |
| 2014/0121459 A1 | 5/2014 | Hoeg et al. | |
| 2014/0121495 A1* | 5/2014 | Dempsey | A61N 5/1064 600/411 |
| 2015/0077112 A1 | 3/2015 | Otazo et al. | |

OTHER PUBLICATIONS

Bhatnagar, P., et al., "Functional Imaging for Radiation Treatment Planning, Response Assessment, and Adaptive Therapy in Head and Neck Cancer", RadioGraphics, Nov.-Dec. 2013, 33(7):1909-1929.

Choi, Y.J., et al., "Pseudoprogression in patients with glioblastoma: added value of arterial spin labeling to dynamic susceptibility contrast perfusion MR imaging", Acta Radiologica, 2013, 54(4):448-454.

Haack, S., et al., "Apparent diffusion coefficients in GEC ESTRO target volumes for image guided adaptive brachytherapy of locally advanced cervical cancer", Acta Oncologica, 2010, 49(7):978-983.

Kondziolka, D., et al., "The biology of radiosurgery and its clinical applications for brain tumors", Neuro-Oncology, 2015, 17(1):29-44.

Kumar, A.J., et al., "Malignant Gliomas: MR Imaging Spectrum of Radiation Therapy- and Chemotherapy-induced Necrosis of the Brain after Treatment", Radiology, Nov. 2000, 217(2):377-384.

Metcalfe, P., et al., "The Potential for an Enhanced Role for MRI in Radiation-therapy Treatment Planning", Technology in Cancer Research and Treatment, Oct. 2013, 12(5):429-446.

Mitsuya, K., et al., "Perfusion weighted magnetic resonance imaging to distinguish the recurrence of metastatic brain tumors from radiation necrosis after stereotactic radiosurgery", Journal of Neuro-Oncology, 2010, 99(1):81-88.

Rossi Espagnet, M.C., et al., "High-Resolution DCE-MRI of the Pituitary Gland Using Radial k-Space Acquisition with Compressed Sensing Reconstruction", American Journal of Neuroradiology, Aug. 2015, 36(8):1444-1449.

Zach, L., et al,. "Delayed contrast extravasation MRI: a new paradigm in neuro-oncology", Neuro-Oncology, 2015, 17(3):457-465.

Zach, L., et al., "Delayed Contrast Extravasation MRI for Depicting Tumor and Non-Tumoral Tissues in Primary and Metastatic Brain Tumors", PLoS ONE, Dec. 2012, 7(12):e52008, 17 pages.

Extended European Search Report for European Patent App. No. 15853193.9, dated May 4, 2018, 7 pages.

\* cited by examiner

METHOD TO SELECT RADIATION DOSAGE FOR TUMOR TREATMENT BASED ON CELLULAR IMAGING

CROSS-REFERENCE TO RELATED APPLICATIONS

This application is a continuation-in-part of International Application PCT/US2015/056263 filed Oct. 19, 2015, which claims the benefit of priority to U.S. Provisional Patent Application No. 62/066,265 filed Oct. 20, 2014, the contents of which are hereby incorporated by reference in their entirety.

FIELD OF THE INVENTION

The present invention generally relates to the treatment of tumors using radiation.

BACKGROUND

Health care professionals commonly use radiation to treat both benign and malignant tumors. In general, health care professionals determine the amount of radiation (the 'dose') to be used based on several different factors. These factors include prior experience; available data about clinical outcomes for tumor responses; tumor volume; safety data regarding radiation received by adjacent body tissue; other available treatment options that could affect the use of higher or lower doses of radiation, and pathological information on tumor cell appearance and the rate of cell division, i.e., mitoses, which requires obtaining a biopsy tissue sample.

Many forms of radiation delivery are image-guided. Available imaging approaches include magnetic resonance imaging ("MRI"); computed tomography ("CT"), x-ray imaging, and positron emission tomography ("PET"), among others. Generally speaking, the images acquired via the aforementioned techniques are typically obtained on or shortly before the day that the radiation dose is administered to the patient.

SUMMARY

In one implementation, a method for treating a target in a treatment subject with radiation is provided. The method includes acquiring non-anatomic imaging information relating to the target based on multiple MRI and/or PET contrasts to determine the properties of the target individual tumor. The non-anatomic imaging information is acquired from at least one imaging marker that reflects at least one of the metabolic, physiological, or histological features of the individual tumor. The method further includes computing a radiation dose based at least in part on the imaging information.

In one implementation, an apparatus for providing a radiation dose to a target in a treatment subject is provided. The apparatus includes a dosage determination module configured to communicate with an imaging system from which imaging information of the target is derived. The dosage determination module is further configured to analyze the imaging information obtained from the imaging system, and determine the radiation dose based on the imaging information.

In one implementation, a non-transitory computer-readable memory having instructions thereon is provided. The instructions include instructions for acquiring imaging information relating to a target from at least one of metabolic imaging and cellular imaging of the target, and instructions for computing a radiation dose based at least on the imaging information.

Other variants of the aforementioned implementations include corresponding systems, apparatuses, and computer-readable media. The implementations do not simply depend on general characteristics of tumor type, clinical experience, prior or concurrent therapies, anatomical imaging features or even histological information from a prior tissue biopsy or biopsies. Rather, additional imaging information is employed that more closely correlates to individual tumor metabolic and histological features to determine therapy.

Additional features, advantages, and embodiments of the present disclosure are apparent from consideration of the following detailed description, drawings, and claims. Moreover, it is to be understood that both the foregoing summary of the present disclosure and the following detailed description are exemplary and intended to provide further explanation without limiting the scope of the present disclosure and the claims.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting of its scope, the disclosure will be described with additional specificity and detail through use of the accompanying drawings, in which:

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Current state of the art medical practice uses images obtained via MRI, CT, x-ray, and PET, etc. solely to provide anatomic information to aid in radiation treatment. For example, such images may be helpful to indicate the shape, location and volume of a tumor, and may also indicate the proximity to the tumor of other structures relevant for decision making by health care professionals. However, imaging information regarding tumor metabolic and histological characteristics is presently not utilized to determine an appropriate dose of radiation.

Furthermore, computer software is used to help plan the radiation profile—i.e., to determine the 'shape' of the radiation dose to be supplied—and to calculate the dose(s) to target or adjacent tissues. However, software is presently not designed or used to determine an appropriate dose of radiation using imaging information from the inherent metabolic and histological characteristics of a tumor. The non-limiting implementations summarized above utilize imaging information to guide the selection of an appropriate dose of radiation. More specifically, the implementations summarized above utilize imaging information for the cellular characteristics of a patient's own tumor to aid in determining the radiation dose to treat the patient's tumor.

As described herein, imaging information from a patient is used to provide individualized radiation treatment for that patient's tumor(s). More particularly, any combination of metabolic and/or cellular imaging is used to determine appropriate doses of radiation for treating tumors. In contrast from approaches that primarily use data based on the treatment of other patients, the approach of some implementations employs data derived specifically from the patient whose tumor is being treated. Further dose planning and administration may be specifically tailored not only for separate individual tumors with different metabolic or cellular characteristics, but also within individual tumors with heterogeneous imaging characteristics.

In some implementations, the patient's own data is used without reference to data from any other patient populations. However, in some implementations, the patient's own data is used in tandem with information derived from the care of other patients, where such information does not necessarily include metabolic and/or cellular imaging results. For example, the radiation dose may be determined based on an algorithm that assigns weighting factors to the patient's own data and to the data from other patients. Furthermore, in some implementations, the radiation dose is determined based on imaging data from the patient herself and based on imaging data from wider patient populations.

Figure 1:
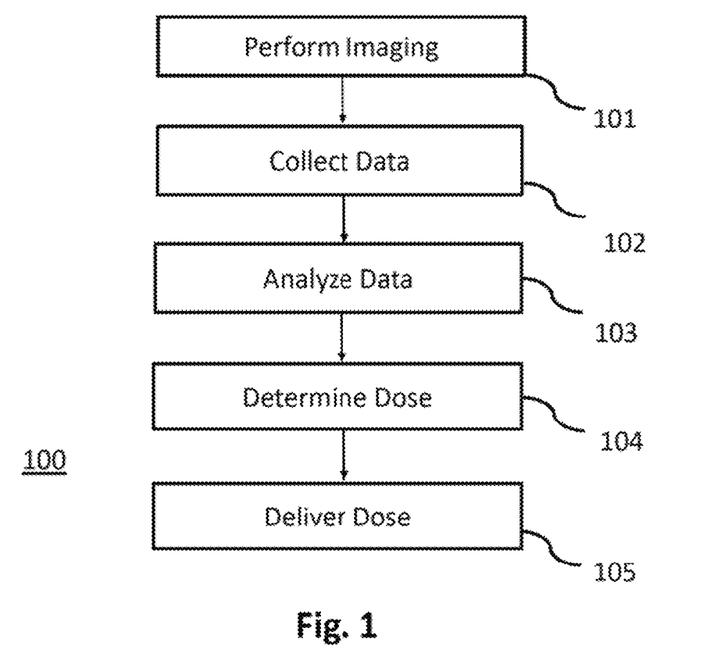
FIG. 1 depicts a method of determining a radiation dose based on patient imaging information in accordance with an illustrative implementation.

FIG. 1 illustrates a method 100 for selecting a radiation dose for treating a tumor (also referred to herein as an object of interest or a target) according to an implementation. The method 100 includes imaging a patient with a tumor. More specifically, the method 100 includes determining an imaging approach to image a patient's tumor and performing the imaging (101). For example, diffusion weighted MRI may be determined as a feasible imaging approach for a given patient. The imaging comprises measuring the specific histologic characteristics of the tumor, such as extracellular matrix, cellular density and organization. The method 100 further includes, during and/or as a result of the imaging process, acquiring at least one of metabolic and cellular information (102). The collection of additional MRI sequences and/or PET contrasts may be incorporated into dose planning.

Following the data acquisition, the method 100 further includes analyzing the imaging data (103). More specifically, the data is analyzed to facilitate selection of an appropriate dose of radiation (104). The dose is selected so as to elicit an intended response in the tumor. For example, the dose selected may be expected to cause the tumor to respond by shrinking to a certain percentage of its former size within a given time period. The determination of an appropriate dose may take into account a plurality of factors, including the following factors, taken separately or in any combination: patient safety, adjacent internal structures, malignancy, patient age, and the patient's prior radiation exposure. Once the dosage is determined, the method 100 may further include administering the dose (105).

In one implementation, the patient's tumor is measured using the apparent diffusion coefficient ("ADC") obtained from diffusion weighted MRI. For example, consider a patient whose breast cancer has spread to her brain. Such a patient may have a tumor that is 1.5 cm in diameter (and may have other tumors as well). The patient's medical team may decide to treat the 1.5 cm diameter tumor with stereotactic radiosurgery, which entails delivering image-guided precision radiation to the tumor during a single session. Conventional approaches may simply dictate that the patient be given a tumor margin dose of 18 gray (Gy) in such circumstances.

In contrast to conventional approaches, in the implementation described herein, the patient's own imaging data may be used to adjust the radiation dose. For example, the patient's tumor may be imaged using diffusion weighted MRI, and an ADC map may be generated based on the imaging. The ADC may indicate such cancer-related factors as cell density, cell differentiation and reticulin density, among other things. By way of illustration, an ADC of $0.8 \times 10^{-3}$ mm$^2$/s is generally indicative of a more aggressive malignant cell population. Based on an ADC of $0.8 \times 10^{-3}$ mm$^2$/s, the patient's radiation dose may be increased to 22 Gy. If, on the other hand, the patient had already received prior treatment and the ADC was $1.0 \times 10^{-3}$ mm$^2$/s, indicating a less aggressive cell population, then the radiation dose could be adjusted downward, for example, to 16 Gy. Hence, in this implementation, the radiation dose is inversely correlated with the tumor ADC.

In another implementation, the patient's tumor is measured using the ADC obtained from diffusion weighted MRI. More particularly, a method of determining a radiation dose based on cellular imaging may be used to determine a dose for a patient suffering from melanoma skin cancer, for example. The patient's melanoma skin cancer may have spread, resulting in a 1.5 cm diameter tumor in the patient's brain. The patient may receive stereotactic radiosurgery to treat this tumor during a single session. Conventional approaches entail, based on the tumor size and location, delivering a tumor margin dose of 20 Gy. In contrast, the present implementation does not determine the dose based solely on information derived from prior experience. Rather, the patient undergoes imaging, specifically, diffusion weighted imaging. An ADC map is produced that may be $0.8 \times 10^{-3}$ mm$^2$/s, indicating a more aggressive malignant cell population. Accordingly, based on the ADC map, the patient's dose would be increased to 24 Gy, for example. Conversely, if the ADC map were $1.0 \times 10^{-3}$ mm$^2$/s, indicating a less aggressive population—here, because the patient received prior treatment of some sort, for example—then the radiation dose would be lowered to 18 Gy.

In some implementations, ADC (or other imaging biomarkers, beyond conventionally-used anatomic information) may be tailored to specific individual tumors in a patient or within specific regions of an individual tumor. For example, many patients with metastatic cancer have multiple intracranial metastases in different anatomic locations—these tumors also may have different ADC values reflecting different local metabolic and histologic features, or different malignant clonal populations. Instead of focusing on anatomic information alone, the techniques described herein provide the treating physician with additional information that may lead to different relative doses to different tumors in the same patient. For example, in a patient with metastatic breast cancer to the left thalamus, a previously irradiated 1 cm spherical tumor may contain two regions with substantially different ADC values. The small area with a low ADC could represent a recurrent or more aggressive residual tumor that warrants the treating physician altering the dose profile to provide more radiation to that region.

Although in some circumstances, low ADC may generally correspond to a more aggressive tumor warranting a higher radiation dose per treatment, other relationships between specific imaging biomarkers and radiation treatment are yet to be established. Potentially, multi-factorial weighted algorithms may be developed for specific patient populations, tumor types and/or individual tumor characteristics to determine which imaging property or properties—anatomic, metabolic and/or histological features, for example, and taken in the context of the treating physician's experience—should be more influential in the ultimate treatment plan.

In the implementations described above, determinations of the radiation dosages are made based on information derived from cellular and/or metabolic imaging of the patient whose tumor is being treated. In some implementations, radiation dosage determinations may be made based on such information, as well as on other quantitative MRI determinants. For example, besides quantitation of ADC illustrated here, additional quantitative maps of magnetic susceptibility, diffusion kurtosis, anisotropy, track density, proton density, $T_1$ and $T_2$ values, $^{18}F$-labeled fluorodeoxyglucose uptake or other quantitative MRI and PET parameters may be used. Other implementations may use different MRI contrasts and/or parameters from those listed herein. Moreover, various forms of imaging that reflect tissue cellular and physiological environments may be used, including MRI, CT, PET, etc.

Further, these values may be assessed within the tumor and/or adjacent structures for treatment planning. For example, if diffusion anisotropy or track density is high in the normal tissues along the medial margin of the tumor, this may be an area where the tumor margin dose should be lower to reduce morbidity from the treatment. In some implementations, the dosage determinations may be made based on anatomic imaging information and some or all of these various other determinants, in any combination. Additionally, MRI parameters besides ADC reflect the tissue environment may be informative for treatment planning. Further, information outside the tumor from these MRI contrasts may also be used to affect planning doses for the tumor. Further, such MRI parameters also may have a specific role in planning dosages when they reflect a) individual-specific increased susceptibility to irradiation injury and/or b) a tissue region already significantly affected by prior stereotactic radiosurgery (e.g., gamma knife radiosurgery ("GKRS")) or other treatments in this region (and hence more vulnerable to injury). Thus, information that is derived outside of the tumor can be used in selecting a dose.

In some implementations, the dosage determinations may be made based on imaging information and various other determinants. In some implementations, radiation dosages for at least one treatment session are determined based on comparing real-time, imaging-based cellular information to clinical outcomes from published data from patient populations. For example, if the cellular information suggests that a tumor cell density is average, and the clinical outcomes for a given type and size of tumor prompt selection of a dose of 18 Gy, then a determination may be made that no significant adjustment of dosage is needed. If the patient is receiving radiation treatment over multiple sessions, and appears to be less responsive to treatment than would be expected based on clinical outcomes, then a higher dose may be administered.

The aforementioned implementations describe imaging of relatively small tumors for patients with cancers that have spread to their brains. It should be understood, however, that the techniques of the present invention may be applied to a plurality of tumors located throughout the body. Furthermore, the techniques described herein have applicability to radiation treatment for numerous forms of cancer and are not limited to metastasized breast cancer and melanoma, as in the foregoing examples. By way of further illustration, some implementations allow for radiation planning in various body regions and may incorporate any combination of magnetic susceptibility, diffusion kurtosis, anisotropy, track density, proton density, $T_1$ and $T_2$ values, perfusion characteristics, $^{18}F$-labeled fluorodeoxyglucose uptake, CT derived parameters, CT perfusion parameters, MRI derived parameters and PET derived parameters. Other embodiments may use different MRI contrasts and/or parameters from those listed herein. In addition, various forms of imaging that reflect tissue cellular and physiological environments may be used, including MRI, CT, PET, etc.

The following are examples of the CT derived parameters, CT perfusion parameters, MRI derived parameters and PET derived parameters mentioned above. CT derived parameters of cellular physiology (based on conventional or dual-energy CT) which may be used for surgical planning include attenuation or Hounsfield units, iodine content, calcification or mineralization content and "monoenergetic plus" values (derived from curves based on attenuation vs various monoenergetic CT radiation energies). CT perfusion parameters may be used for stereotactic radiosurgery treatment planning, including permeability, cerebral blood volume, cerebral blood flow, mean transit time, time-to-peak, and time to peak of the deconvolved tissue residue function. MRI derived parameters of cellular physiology that may be used for stereotactic radiosurgery planning include mean diffusivity or apparent diffusion coefficient; mean kurtosis; radial and axial kurtosis; fractional, radial or general anisotropy; axial and radial diffusivity; axonal watter fraction; tortuosity; proton density, $T_{1rho}$, $T_1$ and $T_2$ values; MRI perfusion parameters estimated from DSC, DCE or ASL techniques including permeability, cerebral blood volume, cerebral blood flow, mean transit time, time-to-peak; chemical exchange saturation transfer (CEST) contrast, and susceptibility or quantitative susceptibility mapping. PET derived parameters may include standard uptake values for various radiotracers including the glucose analogue 2-deoxy-2-[18F]fluoro-D-glucose (18F-FDG), radiolabeled amino acids (e.g., 11C-MET, 18F-FET, 18F-FDOPA), nucleoside analogue 3'-deoxy-3'-fluorothymidine (18F-FLT), hypoxia imaging agents, [11C]choline, [11C]acetate, and the 68Ga-labeled somatostatin receptor ligands DOTATOC and DOTATATE.

Figure 2:
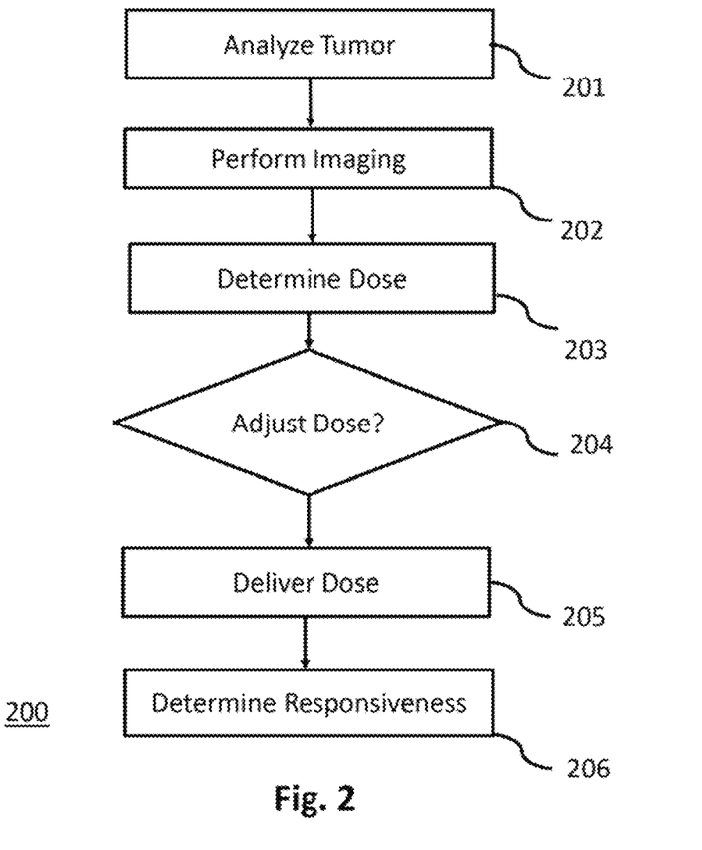
FIG. 2 depicts a method of determining a radiation dose based on patient imaging information in accordance with an illustrative implementation.

In one implementation, a method 200 is provided for determining a radiation dose for treating a tumor. The method 200 differs from the method 100 in certain aspects, as will be described below. The method 200 serves for verification and validation of radiation doses that are ascertained based on clinical population data. The method 200 includes categorizing a tumor in accordance with factors such as tumor size, cancer type, and tumor location (201). The method 200 further includes performing imaging so as to generate an ADC map as described above (202). The method 200, in contrast to the method 100, involves obtaining a standard dose recommendation derived from clinical population data (203). Next, the method 200 includes obtaining a personalized recommendation for the radiation dose based at least on the ADC (204). In other words, the data obtained for the personalized recommendation does not include the clinical population data used for obtaining the standard dose recommendation at (203).

Further, the method 200 involves comparing the personalized and standard recommendations (204). If the comparison indicates a significant discrepancy between the personalized and standard recommendations, the health care professional (e.g., the treating physician) may be alerted with a sign or message that further evaluation is warranted. The health care professional may then determine whether to increase or decrease the standard recommended dose based on the discrepancy. For example, the sign or message may be provided when the deviation or discrepancy exceeds a predetermined threshold. In this manner, the dosage may be altered based on the personalized recommendation, and then delivered to the patient (205). If there is no sizeable discrepancy, then the dose is delivered to the patient without adjustment (205). Once the dose is delivered, the method 200 further includes tracking data relating to tumor responsiveness (206) and aggregating a data set including imaging information and outcomes.

As mentioned above, the method 100 includes analyzing imaging data which may be obtained according to various techniques, and such data may be used to facilitate selection an appropriate dose of radiation (104).

In at least one implementation, imaging data is obtained before and after a surgical procedure, such as stereotactic radiosurgery (SRS). While stereotactic radiosurgery techniques such as GKRS can be generally effective for treating metastases (e.g., intracranial metastases), such techniques generally rely almost solely on post-contrast MRI, which allows only limited tumor characterization. Speaking generally, it is difficult to distinguish tumor recurrence from radiation-induced change utilizing imaging following stereotactic radiosurgery. At least one implementation allows for evaluation of metastases before and after stereotactic radiosurgery, to achieve higher temporal resolution and more complete coverage. In particular, in at least one implementation, golden-angle radial sparse parallel (GRASP) MRI can be used, for example, to provide high resolution imaging of tumors, as described in Fatterpekar, G M et al., "Permeability Imaging of Parotid Tumors with Golden-Angle radial Sparse Parallel MR Imaging (GRASP)," *Clinical Head and Neck Imaging* (2016), 65: 44-45. For example, GRASP MRI allows for imaging of cortical lesions, both before and after stereotactic radiosurgery, with substantially higher resolution and coverage.

The benefits of GRASP MRI have been experimentally confirmed via imaging performed on 32 patients collectively having 56 metastases. Imaging data was obtained from 20 of the patients collectively having 36 lesions, 66±20 days after stereotactic radiosurgery (here, GKRS). Lesions which were under 0.5 cm, lesions with hemorrhaging, or those with prior surgery or radiotherapy were excluded. Regions of interest were drawn in a solid enhancing tumor with image co-registration. Permeability parameters including wash-in, wash-out, peak and area under the curve (AUC) for contrast enhancement were compared with unpaired t-tests. Metastatic lesions showed a 41.3% reduction in AUC (P=0.055) and 51.1% reduction in wash-in kinetics (P<0.0001) following stereotactic radiosurgery. Melanoma metastases had 84.5% greater AUC (P=0.1248) and 28.1% shorter wash-in kinetics (P=0.2024) compared to lung metastases at baseline. After stereotactic radiosurgery, melanoma metastases demonstrated larger reductions in AUC (39.1% vs 20.1%, P=0.1881). Substantial reductions in AUC and wash-in were observed for intracranial metastases approximately 60 days following stereotactic radiosurgery. Such reductions may be attributable to the destruction of tumor blood vessels and permeability.

Further, in at least one implementation, tumor recurrence may be evaluated using permeability parameters derived from GRASP MRI.

Figure 3A:
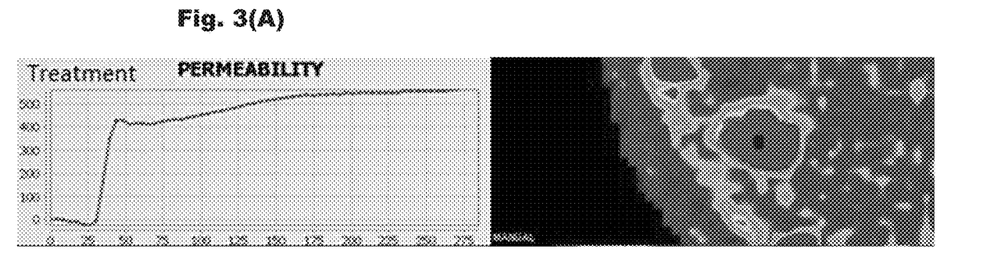
FIG. 3A depicts imaging results in accordance with an illustrative implementation, at the time of treatment.
Figure 3B:
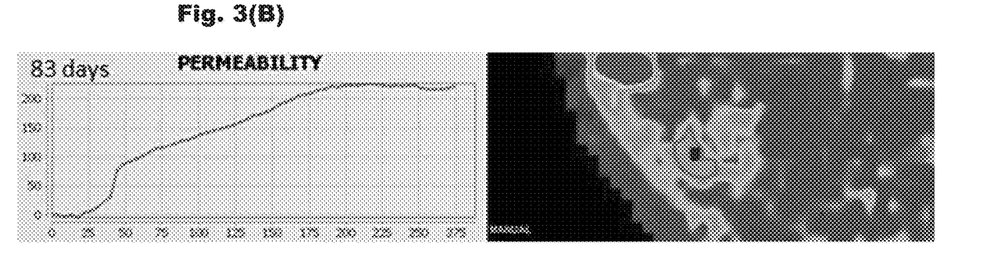
FIG. 3B depicts imaging results in accordance with an illustrative implementation, at 83 days after treatment.
Figure 3C:
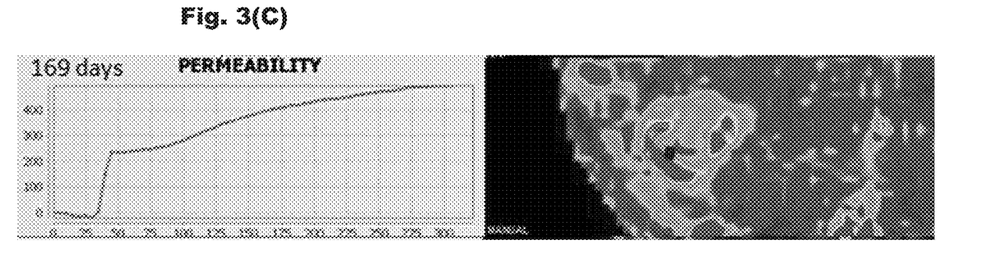
FIG. 3C depicts imaging results in accordance with an illustrative implementation, at 169 days after treatment.
Figure 3D:
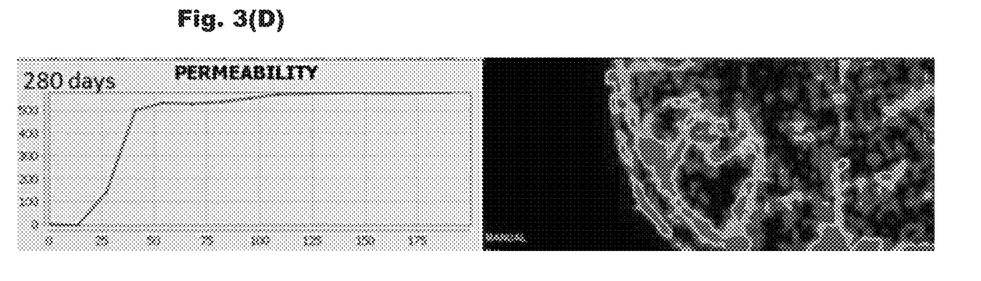
FIG. 3D depicts imaging results in accordance with an illustrative implementation, at 280 days after treatment.

FIGS. 3A-3D depict experimental data immediately before stereotactic radiosurgery (in these experiments, GKRS), using permeability parameters derived from GRASP MRI. A 1.5×1.2 cm sized heterogeneously enhancing lesion was treated using stereotactic radiosurgery and imaged (FIG. 3A). The lesion was imaged subsequently at 83 days (FIG. 3B), 169 days (FIG. 3C), and 280 days (FIG. 3D) using GRASP. GRASP images were post processed using Olea Sphere software (Olea Medical, LaCiotat). An enhancement-time graph (based on region-of-interest, ROI) analysis of the solid component of the lesions was performed, before and after treatment.

Conventional imaging demonstrated a continued increase in the size of the heterogeneously enhancing metastatic lesion. In contrast, GRASP imaging showed an initial rightward shift of the enhancement time curve, which may reflect an increasing breakdown of the blood-brain barrier following stereotactic radiosurgery. Subsequent GRASP assessment, however, demonstrated a leftward shift of this curve, as reflected in FIGS. 3C-3D in particular. This leftward shift of the curve likely reflects neoangiogenesis and is therefore suggestive of tumor recurrence. A biopsy later confirmed the tumor recurrence indicated by the GRASP imaging.

As GRASP imaging allows for evaluation of the entire brain, GRASP imaging may be particularly informative for intracranial imaging, because metastatic lesions may be scattered throughout the brain and close to the cortex. For these reasons, at least one exemplary implementation includes determining a treatment dosage based on information from at least one GRASP image.

Figure 4:
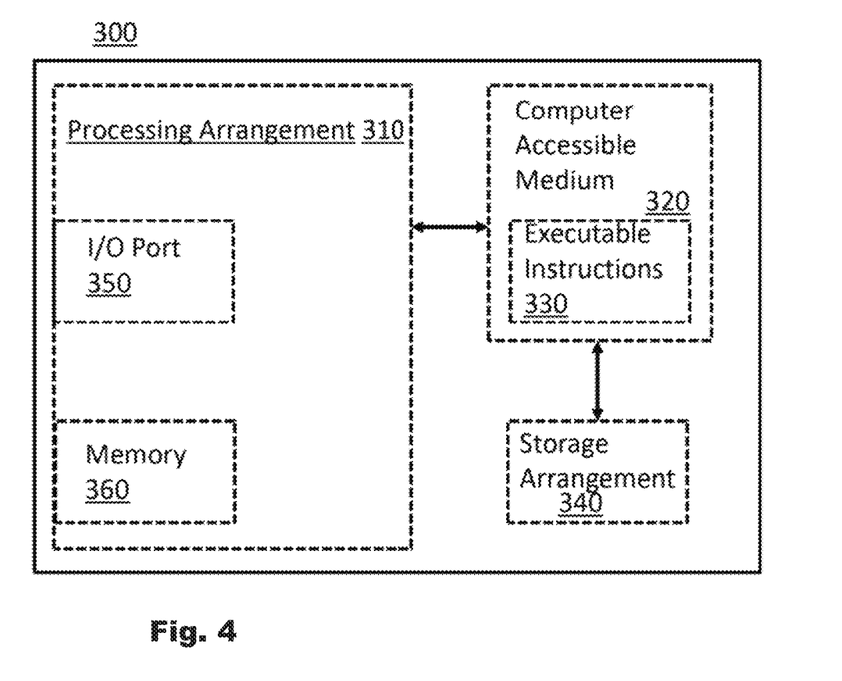
FIG. 4 depicts a computer system for the selection of radiation dosage for tumor treatment, according to an implementation.

In one implementation, a computer system 300 is provided. As shown in FIG. 4, the computer system 300 includes a computer-accessible medium 320 (e.g., as described herein, a storage device such as a hard disk, floppy disk, memory stick, CD-ROM, RAM, ROM, etc., or a collection thereof) which may be provided, for example, in communication with a processing arrangement 310. The computer-accessible medium 320 may be a non-transitory computer-accessible medium. In some implementations, the system 300 may include software for planning radiation treatment. Such software may include instructions for planning the characteristics of the radiation to be provided and for calculating the radiation dose to the tumor or adjacent tissues.

The computer-accessible medium 320 can contain executable instructions 330 thereon. For example, in some implementations, instructions are provided for planning a course of radiation treatment. Instructions for planning a course of radiation treatment may include instructions for carrying out measurements of cellular density, instructions to formulate a dosage recommendation, and instructions to store data regarding historical dosages and tumor responsiveness, among others. In some implementations, the instructions for formulating a dosage recommendation may base the recommendation at least on cellular imaging data. In some implementations, the instructions for formulating the dosage recommendation may base the recommendation on cellular imaging data and at least one of a tumor volume, the presence or absence of edema (an edema indicator), and the blood-brain barrier integrity.

In one implementation, the computer-accessible medium 320 contains executable instructions 130 thereon for determining a radiation dose based on imaging techniques. The imaging techniques may include, for example, any combination of MRI quantitative maps of metabolites such as choline, $T_1$ and $T_2$ relaxation parameters, susceptibility, track density, and diffusion kurtosis. Susceptibility is an MRI measure of the presence of microscopic magnetic materials such as blood products, iron or calcium. Track density is a measure of the number of probabilistic tractography streamlines running through a region and correlates with axonal density in the region. Furthermore, in some implementations, the instructions 330 include instructions for serially measuring cellular imaging responses before and after irradiation. The serial measurements thereby collected may be used to study the tumor response to radiation and evaluate the efficacy of the treatment. Different MRI contrasts and/or parameters from those listed herein may be used. Moreover, various forms of imaging that reflect tissue cellular and physiological environments may be used, including MRI, CT, PET, etc.

In addition or alternatively, a storage arrangement 340 can be provided separately from the computer-accessible medium 320, which can provide the instructions to the processing arrangement 310 so as to configure the processing arrangement to execute certain exemplary procedures, processes and methods, as described herein, for example. The instructions may include a plurality of sets of instructions. For example, in some implementations, the instructions may include instructions for determining at least one dose of radiation to be delivered to a tumor during at least one treatment session. The instructions may further include instructions for building a library of imaging information based on metabolic and/or cellular imaging results from a plurality of patients.

System 300 may also include a display or output device, an input device such as a key-board, mouse, touch screen or other input device, and may be connected to additional systems via a logical network. Many of the implementations described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols.

Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Implementations may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various implementations are described in the general context of method steps, which may be implemented in one embodiment by a program product including computer-executable instructions, such as program code, executed by computers in networked environments, for example. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention may be accomplished with programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity. Use of the masculine pronoun is intended to include both the feminine and gender-neutral pronouns, and vice versa.

The foregoing description of illustrative implementations has been presented for purposes of illustration and of description. It is not intended to be exhaustive or limiting with respect to the precise form disclosed, and modifications and variations are possible in light of the above teachings or may be acquired from practice of the disclosed implementations. Therefore, the above implementations should not be taken as limiting the scope of the invention.

The invention claimed is:

1. A method for treating a target in a treatment subject via radiation, the method comprising:
   acquiring non-anatomic imaging information relating to the target from at least one imaging marker for internal tumor cellular features that reflects a histological feature of the target, the histological feature comprising at least one of cellular characteristics, extracellular matrix, cellular density, or organization;
   computing, by a computer processor, a radiation dose based on the non-anatomic imaging information; and
   delivering the radiation dose based on the non-anatomic imaging information to the target in the treatment subject.

2. The method of claim 1, further comprising:
   delivering the radiation dose to the treatment subject during a same treatment session in which the imaging information is acquired.

3. The method of claim 1, further comprising:
   wherein the non-anatomic imaging information is apparent diffusion coefficient information obtained from diffusion weighted MRI; and
   measuring cellularity of the target based at least on the apparent diffusion coefficient (ADC) obtained from the non-anatomic imaging information;

wherein the computing of the radiation dose is based upon the measured cellularity obtained from the non-anatomic imaging information.

4. The method of claim 1, wherein computing the radiation dose comprises computing the radiation dose based on the imaging information and at least one of mapping of metabolites, mapping of relaxation parameters, a susceptibility value, a track density value, a diffusion kurtosis value, anisotropy, a proton density value, $T_1$ and $T_2$ values, an $^{18}$F-labeled fluorodeoxyglucose uptake, a CT derived parameter, a CT perfusion parameter, an MRI derived parameter or a PET derived parameter.

5. The method of claim 1, wherein acquiring the imaging information comprises performing diffusion weighted MRI.

6. The method of claim 1, wherein the imaging information indicates at least one of a target shape, a target location, or a target volume.

7. The method of claim 1, further comprising:
monitoring responsiveness of the target to the delivered radiation dose.

8. The method of claim 1, further comprising:
comparing the computed radiation dose to a radiation dose determined based on at least one of clinical outcome data, tumor volume, safety data, or pathologic information.

9. The method of claim 1, wherein the target is a tumor, the method further comprising:
acquiring anatomic imaging information relating to a structure adjacent to the target.

10. The method of claim 1, wherein the target is a tumor, the method further comprising:
acquiring anatomic imaging information relating to a structure adjacent to the target; and
delivering the radiation dose based on the non-anatomic imaging information and the anatomic imaging information to the target in the treatment subject.

11. An apparatus for providing a radiation dose to a target in a treatment subject, the apparatus comprising:
a computer system configured to communicate with an imaging system from which at least non-anatomic imaging information of the target is acquired from at least one imaging marker for internal tumor cellular features that reflects a histological feature of the target, the histological feature comprising at least one of cellular characteristics, extracellular matrix, cellular density, or organization, the computer system having nontransitory memory having instructions that cause a processor to:
analyze the non-anatomic imaging information acquired from the imaging system,
compute the radiation dose based on the non-anatomic imaging information; and
cause a radiation delivery mechanism to deliver the radiation dose based on the non-anatomic imaging information to the target in the treatment subject.

12. The apparatus of claim 11, further comprising:
the radiation delivery mechanism configured to deliver the radiation dose to the target during a same treatment session in which the imaging information is acquired.

13. The apparatus of claim 11, wherein the computer system is configured to measure cellularity of the target based at least on an apparent diffusion coefficient (ADC) obtained from the imaging information.

14. The apparatus of claim 13, wherein the radiation dose is computed by evaluating the ADC, a target size, or a target location.

15. The apparatus of claim 11, wherein the radiation dose is computed based on the imaging information and at least one of mapping of metabolites, mapping of relaxation parameters, a susceptibility value, a track density value, a diffusion kurtosis value, anisotropy, a proton density value, $T_1$ and $T_2$ values, $^{18}$F-labeled fluorodeoxyglucose uptake, a CT derived parameter, a CT perfusion parameter, an MRI derived parameter or a PET derived parameter.

16. The apparatus of claim 11, wherein the imaging information is acquired by at least one of MRI, CT, x-ray or PET imaging.

17. The apparatus of claim 11, further comprising:
a data storage module configured to store data indicating the radiation dose, a cellularity measurement prior to delivery of the radiation dose, and a cellularity measurement following delivery of the radiation dose.

18. The apparatus of claim 17, wherein the computer system is configured to evaluate a target response based on the cellularity measurements prior to and following delivery of the radiation dose.

* * * * *